United States Patent
Rommelaere et al.

(10) Patent No.: US 9,861,669 B2
(45) Date of Patent: Jan. 9, 2018

(54) ONCOLYTIC VIROTHERAPY FOR PREVENTION OF TUMOR RECURRENCE

(75) Inventors: Jean Rommelaere, Heidelberg (DE); Zahari Raykov, Heidelberg (DE); Svitlana Grekova, Heidelberg (DE); Irina Kiprijanova, Heidelberg (DE); Karsten Geletneky, Heidelberg (DE); Ute Koch, Epalinges (CH); Marc Aprahamian, Limersheim (FR)

(73) Assignees: Deutsches Krebsforschungszentrum Stiftung des Oeffentlichen Rechts, Heidelberg (DE); Ruprecht-Karls-Universitaet Heidelberg, Heidelberg (DE)

( * ) Notice: Subject to any disclaimer, the term of this patent is extended or adjusted under 35 U.S.C. 154(b) by 0 days.

(21) Appl. No.: 13/376,137

(22) PCT Filed: May 19, 2010

(86) PCT No.: PCT/EP2010/003069
§ 371 (c)(1),
(2), (4) Date: May 29, 2012

(87) PCT Pub. No.: WO2010/139400
PCT Pub. Date: Dec. 9, 2010

(65) Prior Publication Data
US 2012/0237483 A1    Sep. 20, 2012

(30) Foreign Application Priority Data
Jun. 4, 2009  (EP) .................................. 09007432

(51) Int. Cl.
*A61K 35/76*  (2015.01)
*A61P 1/18*   (2006.01)
*A61K 35/768* (2015.01)
*A61K 48/00*  (2006.01)

(52) U.S. Cl.
CPC .. *A61K 35/768* (2013.01); *C12N 2750/14332* (2013.01)

(58) Field of Classification Search
CPC ................... A61K 35/768; C12N 2750/14332
See application file for complete search history.

(56) References Cited

U.S. PATENT DOCUMENTS 7,179,456 B2 * 2/2007 Rommelaere et al. ...... 424/93.1
8,414,883 B2 * 4/2013 Rommelaere et al. ...... 424/93.2
2003/0165465 A1 * 9/2003 Roberts ................ A61K 38/191
                                                   424/93.2
2004/0220124 A1   11/2004 Rommelaere et al.
2012/0213734 A1 * 8/2012 Kiprijanova et al. ....... 424/85.5
2013/0058899 A1 * 3/2013 Marchini et al. ............ 424/93.6

FOREIGN PATENT DOCUMENTS

WO    WO 2006/047301    5/2006

OTHER PUBLICATIONS

Stathopoulos A et al. Therapeutic vaccination against malignant gliomas based on allorecognition and syngeneic tumor antigens: Proof of priciple in two strains of rat. 26: 1764-1772, 2008.*
Moehler, M; Blechacz, B; Rommelaere, J; Cornellis, JJ; Stremmel, W; Galle, PR "Infection, Cytotoxicity and Gene Transfer of Parvovirus H-1 in Human Hepatocellular Carcinoma Cells" Proceedings of the American Association for Cancer Research. 90th Annual Meeting Apr. 10-14, 1999, Abstracts published Mar. 1999, 40, 476pp.(Abstract only).*
Angelova, Assia [Reprint Author]; Galabov, Angel S.; Rommelaere, Jean; Raykov, Zahari "Antitumour Effects of Combined Radio- and Parvovirotherapy in N-Ras-positive Tumour Cells." Dokladi na Bolgarskata Akademiya na Naukite, 2007, 60(8), pp. 879-882. (Abstract only).*
Geletneky, K, et al "Phase I/IIa study of intratumoral/intracerebral or intravenous/intracerebral administration of Parvovirus H-1 (ParvOryx) in patients with progressive primary or recurrent glioblastoma multiforme: ParvOryx01 protocol" BMC Cancer, Mar. 21, 2012, 12:99, 9 pages.*
"186 Poster Complete remission of advance autologous intracranial gliomas by oncolytic Parvovirus H-1", European Journal of Cancer, vol. 3, No. 2, Oct. 1, 2005, p. 53, XP005132303.
Zahari Raykov et al., "Carrier cell-mediated delivery of oncolytic parvoviruses for targeting metastases", International Journal of Cancer, vol. 109, No. 5, May 1, 2004, pp. 742-749, XP002554386.
International Search Report for PCT/EP2010/003069 dated Oct. 27, 2010.
Assia L. Angelova et al., Improvement of Gemcitabine-Based Therapy of Pancreatic Carcinoma by Means of Oncolytic Parvovirus H-1PV, Clin Cancer Res 2009; 15(2) Jan. 15, 2009, pp. 511-519.
Wen et al., The New England Journal of Medicine 2008, 359, pp. 492-507.
Tutt et al., Oncolog, MD Anderson's Report to Physicians, 2011, vol. 56, No. 3, pp. 1-3 and 8.
Archavlis et al., BMJ Open 2013, p. 1-9.

* cited by examiner

*Primary Examiner* — Chris R Tate
*Assistant Examiner* — Aaron J Kosar
(74) *Attorney, Agent, or Firm* — Crowell & Moring LLP

(57) ABSTRACT

Described is a parvovirus for preventing recurrence of a tumor, preferably a malignant brain tumor or pancreas tumor.

3 Claims, 4 Drawing Sheets

ONCOLYTIC VIROTHERAPY FOR PREVENTION OF TUMOR RECURRENCE

This application is a national stage of PCT International Application No. PCT/EP2010/003069; filed May 19, 2010, which claims priority under 35 U.S.C. §119 to European Application No. 09007432.9, filed Jun. 4, 2009, the entire disclosure of which is herein expressly incorporated by reference.

The present invention provides a parvovirus for preventing recurrence of a tumor, preferably a malignant brain tumor or pancreatic cancer.

The unsuccessful long-term treatment of malignant tumors is frequently due to tumor recurrence. This is in particular a problem in the therapy of malignant brain tumors. Even when surgical removal of the tumor was successful with no residual tumor to be demonstrated on MRI, more than 90% of patients will develop recurrent tumors within 2 to 3 years after the initial treatment. Current standard strategies to improve this situation include the use of radio-chemotherapy. However, this treatment has only been shown to improve survival by 3 to 4 months but not to alter the rate of tumor relapses or long-term survivors. Although currently various experimental drugs and strategies are under investigation to prolong survival and reduce the rate of tumor recurrence, up to now there are no reports about any major breakthroughs.

Therefore, it is the object of the present invention to provide means for prevention of tumor recurrence.

According to the invention this is achieved by the subject matters defined in the claims. The present invention is based on the applicant's findings that the prevention of spontaneous tumor recurrence and the induction of tumor specific immunity can be achieved by oncolytic virotherapy with parvovirus H-1, exemplified for experimental gliomas and pancreatic cancer. The treatment of tumors with the oncolytic parvovirus H-1 results in the development of tumor-specific immunity. This effect was detected in immunocompetent Wistar-rats bearing intracranial RG-2 gliomas. The induction of tumor specific immunity after successful treatment of brain tumors with parvovirus H-1 has not been demonstrated previously.

To analyze the immunological effects of H-1PV treatment, several separate experiments were performed:

Experiment 1 describes the re-challenge of successfully treated Wistar rats with RG-2 tumor cells. Female Wistar rats (n=7) bearing large intracranial RG-2 gliomas were treated with parvovirus H-1PV (intratumoral injection: n=4; intravenous injection: n=3). After complete tumor remission demonstrated by MRI and a follow-up period of >6 months after successful treatment the animals were re-challenged with RG-2 tumor cells (intracranial injection) and observed for tumor formation including MR imaging. The goal of the experiment was to assess whether the animals were protected from recurrent tumor growth by the first treatment.

Experiment 2 describes the analysis of tumor specific immunological effects after tumor re-challenge in animals after successful parvovirus H-1PV therapy. The goal of this experiment was to assess whether upon intracranial re-challenge with RG-2 cells animals that had been cured from an experimental glioma by H-1PV injection showed a tumor specific immune response. To test this, lymphocytes were harvested from draining lymph nodes and purified. The purified lymphocytes were stimulated with irradiated RG-2 cells, with irradiated and previously H-1PV infected RG-2 cells or with freeze-thawed RG-2 cells. Concanavalin A treatment of lymphocytes served as control to verify specific lymphocyte viability. After 48 hours of exposure to the respective antigen, cells were pulsed with 3H-thymidine and harvested after 72 hours.

Experiment 3 describes the participation of T-cells in the oncosuppressive effect of H-1PV.

Experiment 4 shows that adoptive transfer of tumor specific immune cells to uninfected tumor-bearing rats results in an oncosuppressive effect.

A2: MR 3 days after i.c. treatment with H-1PV demonstrating tumor in remission;

A3: MR 7 days after i.c. treatment with H-1PV with almost complete tumor remission;

A4: MR 150 days after tumor re-challenge with no visible tumor.

Figure 2A:
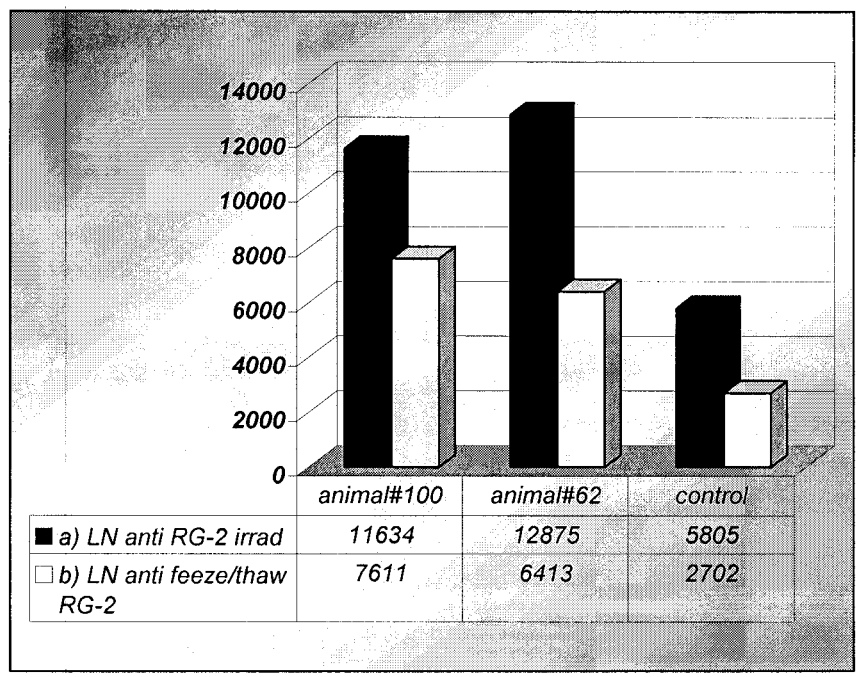

FIG. 2a: Absolute counts (3H Thymidine uptake) after co-cultivation of lymphocytes with tumor-antigens in 2 re-challenged animals LN=lymphocytes from draining lymph nodes FIG. 2b: Relative changes of lymphocyte activity after co-cultivation of lymphocytes with tumor-antigens in 2 re-challenged animals (% difference to control animal)

Figure 3:
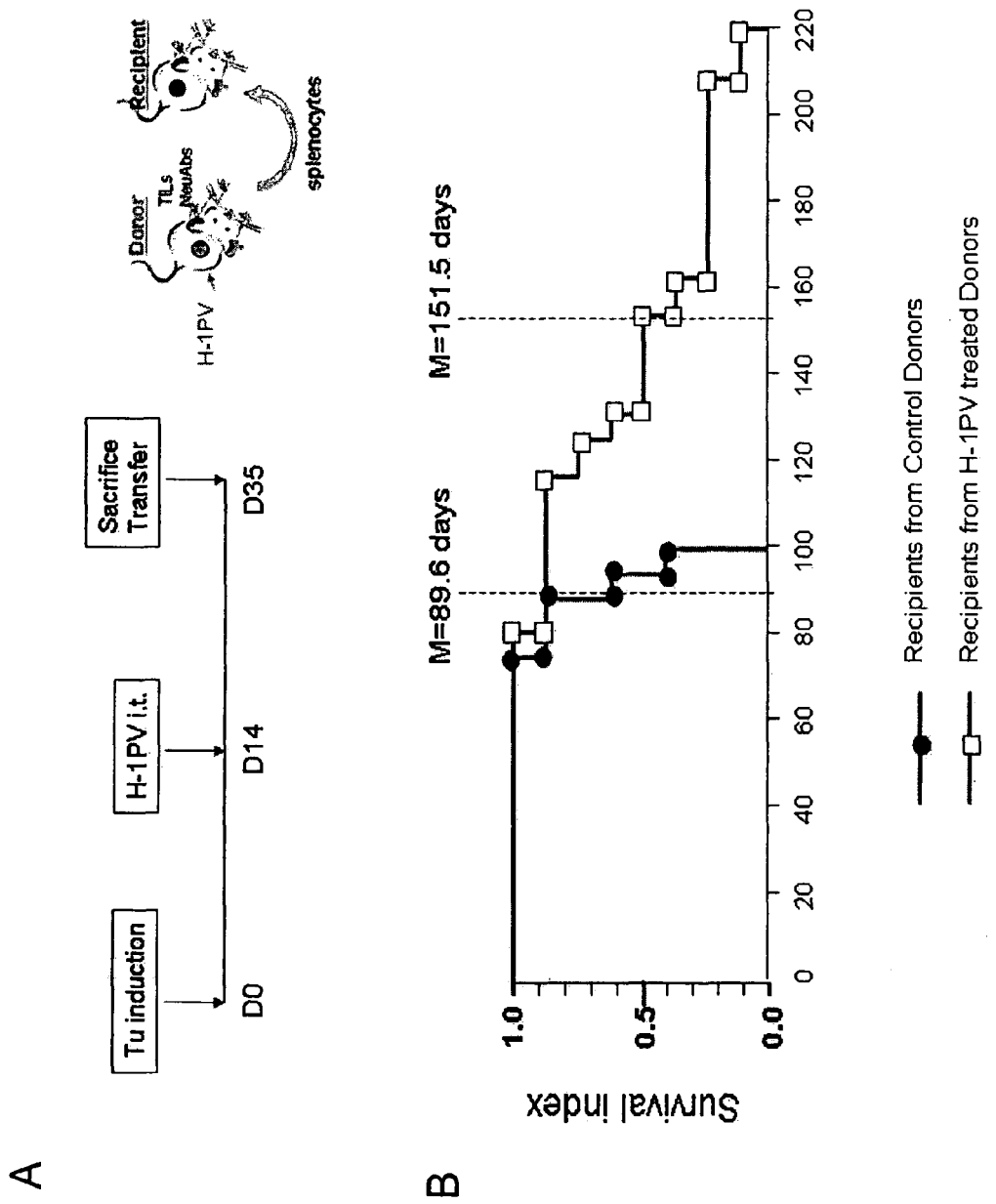

FIG. 3: Adoptive transfer of splenocytes from treated donors into naive recipients (A) Schematic representation of donors' treatment protocol. Rats (n=16) bearing pancreatic tumors were treated either with PBS (n=8) or H-1PV ($1 \times 10^9$ plaque-forming units per animal, n=8) intratumorally. At that time tumors were induced in 16 rats serving as splenocyte recipients.

(B) Survival index of recipient rats 220 days after tumor inoculation. Adoptive transfer was performed 21 days (arrow) after recipient tumor initiation. Rats received splenocytes from PBS controls (closed circles) or H-1PV-treated (open squares) donors.

The present invention provides a parvovirus for use in a method for preventing recurrence of a tumor.

Preferably, said parvovirus (parvotherapeutic agent) is formulated as a pharmaceutical composition, wherein the parvovirus is present in an effective dose and combined with a pharmaceutically acceptable carrier. "Pharmaceutically acceptable" is meant to encompass any carrier which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Additional pharmaceutically compatible carriers can include gels, bioasorbable matrix materials, implantation elements containing the therapeutic agent, or any other suitable vehicle, delivery or dispensing means or material(s). Such carriers can be formulated by conventional methods and can be administered to the subject at an effective dose.

An "effective dose" refers to amounts of the active ingredients that are sufficient to prevent recurrence of a tumor. An "effective dose" may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Administration of the compounds may be effected by different ways, e.g. by intravenous, intratumoral, intraperetoneal, subcutaneous, intramuscular or intradermal administration. The route of administration, of course, depends on the kind of therapy and the kind of compounds contained in the pharmaceutical composition. A preferred route of administration is intravenous administration. The dosage regimen of the parvovirus (parvotherapeutic agent) is readily determinable within the skill of the art, by the attending physician based an patient data, observations and other clinical factors, including for example the patient's size, body surface area, age, sex, the particular parvovirus etc. to be administered, the time and route of administration, the tumor type and characteristics, general health of the patient, and other drug therapies to which the patient is being subjected.

If the parvotherapeutic agent(s) according to the invention comprise infectious virus particles with the ability to penetrate through the blood-brain barrier, treatment can be performed or at least initiated by intravenous injection of the viral therapeutic agent, e.g., H1 virus. A preferred route of administration is intratumoral or, in case of brain tumors, intracranial or intracerebral administration.

As another specific administration technique, the parvotherapeutic agent can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvotherapeutic composition to be injected locally at various times without further surgical intervention. The parvovirus can also be injected into the tumor by stereotactic surgical techniques or by neuronavigation targeting techniques.

Administration of the parvotherapeutic agent can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvotherapeutic agent is from an implanted device constructed and arranged to dispense the parvotherapeutic agent to the desired tumor tissue. For example, wafers can be employed that have been impregnated with the parvotherapeutic composition, e.g., parvovirus H-1PV, wherein the wafer is attached to the edges of the resection cavity at the conclusion of surgical tumor removal. Multiple wafers can be employed in such therapeutic intervention. Cells that actively produce the parvotherapeutic agent, e.g., parvovirus H1, can be injected into the tumor, or into the tumoral cavity after tumor removal.

The therapy according to the invention is useful for the prevention of the recurrence of tumors, in particular brain tumors and pancreas tumors and can, thus, significantly improve the prognosis of said diseases. The increased anti-tumor response by infection with oncolytic parvoviruses combines the direct and specific cytotoxicity of this virus against tumor cells (but not healthy cells) with a secondary and long term anti-tumor activity based on the induction of tumor specific immunity.

In a preferred embodiment of the present invention, the parvovirus is utilized in the prevention of the recurrence of brain tumors such as glioma, medulloblastoma and meningioma. Preferred gliomas are malignant human glioblastomas. However, the therapy according to the present invention is, in principle, applicable to any tumor that can be infected with the parvotherapeutic agent, e.g., parvovirus H-1PV. Such tumors comprise pancreas tumors, prostate tumors, lung tumors, renal tumors, hepatoma, lymphoma, breast tumors, neuroblastoma, colon tumors and melanoma.

The term "parvovirus" or "parvotherapeutic agent" as used herein comprises wild-type viruses, modified replication-competent derivatives thereof, e.g. CpG-armed viruses, as well as related replication-competent or non-replicating viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

In another preferred embodiment of the present invention, the parvovirus of the composition comprises parvovirus H-1 (H-1PV) or a related parvovirus such as LuIII, Mouse minute virus (MMV), Mouse parvovirus (MPV), Rat minute virus (RMV), Rat parvovirus (RPV) or Rat virus (RV).

Patients treatable by the parvotherapeutic agent according to the invention include humans as well as non-human animals. Examples of the latter include, without limitation, animals such as cows, sheep, pigs, horses, dogs, and cats.

Finally, the present invention also relates to the use of parvovirus, e.g., H-1 (H-1PV) or a related parvovirus, e.g., LuIII, Mouse minute virus (MMV), Mouse parvovirus (MPV), Rat minute virus (RMV), Rat parvovirus (RPV) or Rat virus (RV), for the preparation of a pharmaceutical composition for the prevention of the recurrence of a tumor.

Treatment using a parvotherapeutic agent can be combined with further kinds of therapy, e.g., chemotherapy using, e.g., a chemotherapeutic agent like gemcitabine, radiotherapy or immunotherapy.

The below examples explain the invention in more detail.

EXAMPLE 1

Materials and Methods (A) Cell Lines

The rat glioblastoma cell lines RG-2 were grown in DMEM (Sigma-Aldrich, Steinheim, Germany) supplemented with 10% FCS (Biochrom KG, Berlin, Germany) and 1% antibiotics (penicillin, streptomycin; Gibco, Invitrogen Corporation, Karlsruhe, Germany) in a 5% $CO_2$ humidified atmosphere at 37° C. Exponentially growing RG-2 cells to be injected in rat brains were trypsinized and centrifuged (1000 rpm/10 min), and the pellet was resuspended in DMEM without supplements.

(B) Irradiation of RG-2 Cells

Prior to co-cultivating RG-2 cells with lymphocytes the cells were irradiated with 3000 cGy, a dose that was able to stop cellular proliferation.

(C) Parvovirus H-1 (H-1PV) Production and Infection

H-1PV was amplified in human NBK cells and purified on iodexanol gradients as previously described (Faisst et al., J Virol 69 (1995), 4538-43). H-1PV was titrated on NBK indicator cells by plaque assay and further used at multiplicities of infections (MOI) expressed in plaque-forming units (pfu) per cell.

(D) In Vitro Stimulation Assay

This test was used to assay specific activation of lymphocytes by co-cultivating with tumor antigens. LN cells were harvested from draining lymph nodes by mechanical disruption of the lymph node with a syringe plunger and filtration of the debris through a mesh. Phosphate-buffered saline (PBS) solution supplemented with 0.1% bovine serum albumin (BSA; Sigma Chemical Co, St Louis, Mo.) was used for all in vitro manipulations of the lymphocytes. LN cells were seeded at $2.5 \times 10^5$ cells/well in a 96-well round-bottom plate and further cultivated in RPMI 1640 medium supplemented with 10% fetal calf serum, 2 mmol/L glutamine, 50 U/mL penicillin, 50 µg/mL streptomycin, Hepes 25 mM, and 0.05 mmol/L 2-mercaptoethanol. Cultures were incubated in complete RPMI medium at 37° C. and 70 $CO_2$ for 48 hours and 1 µCi [$^3$H] TdR/well was added to each well. At 72 hours cells were harvested onto glass fiber filters (Wallac Oy, Turku, Finland) with a Harvester 96 (TomTec, Orange, Conn.) and counted in a 1205 Beta-Plate reader (Wallac, Gaithersburg, Md.). The results were expressed as the mean CPM±standard deviation (SD) of quadruplicate cultures.

(E) Animal Experiments

All animal experiments were carried out in accordance with institutional and state guidelines.

(F) Intracerebral Implantation of Tumor Cells 8 female Wistar rats (Charles River, Sulzfeld, Germany) that were successfully treated with parvovirus H-1PV between 6 and 12 months prior to the re-challenge experiment (5 rats had received intratumoral treatment, three rats had received intravenous treatment) were used. Female Wistar inbred rats were anaesthetized with Isoflurane (initial dose 2.50, maintenance 1.6%) and mounted to a stereotactic frame. After linear scalp incision, a 0.5 mm burrhole was made 2 mm right of the midline and 1 mm anterior to the coronal suture. The needle of a 10 µl Hamilton syringe was stereotactically introduced through the burrhole into the frontal lobe at a depth of 5 mm below the level of the dura mater, and RG-2 glioma cells (1000000 cells in a volume of 5 µl) were injected over 5 min. The needle was withdrawn slowly, and the burrhole was sealed with bone wax.

EXAMPLE 2

Re-Challenge of Successfully Treated Wistar Rats with RG-2 Tumor Cells

Figure 1:
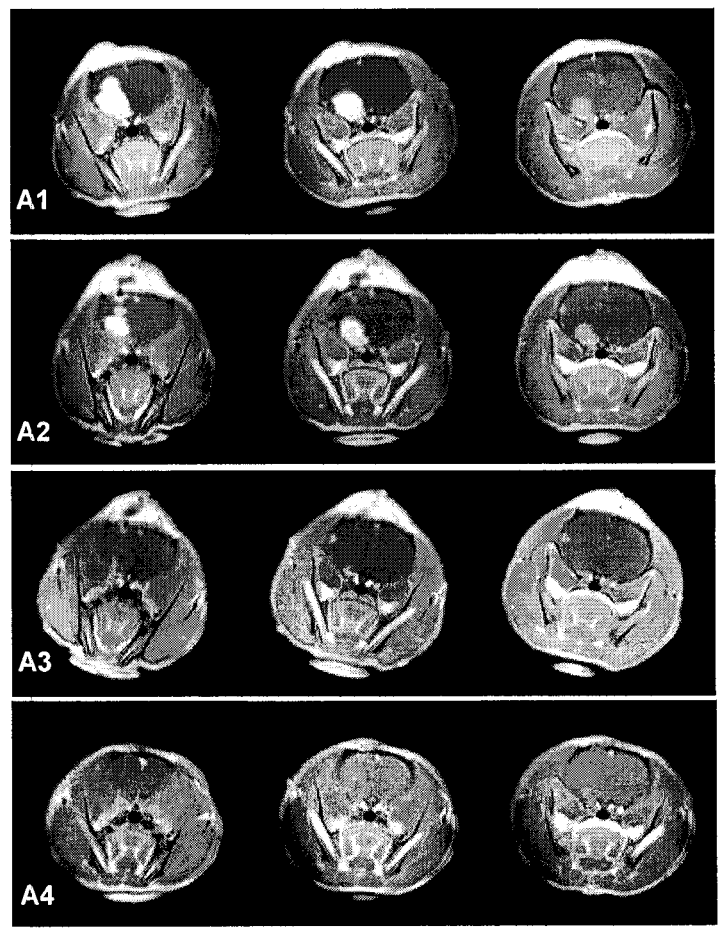
FIG. 1: Example of MR imaging after successful treatment (i.c.) and re-challenge A1: MR (3 sections in cranio-caudal direction) 1 day before H-1PV treatment.

A total of 7 rats had been successfully treated with H-1PV with complete remission of intracranial gliomas. Of these 7 rats, 4 rats had received intracerebral (i.c.) treatment and 3 rats had received intravenous (i.v.) treatment. In i.v. treated rats the intact humoral immune response was demonstrated by the formation of neutralizing antibodies (Table 1). After an observation period of 6 months without regrowth of gliomas rats were re-challenged with intracerebral injection of 100.000 RG-2 tumor cells. 2 control animals were injected with the same number of tumor cells. 0/7 re-challenged animals developed RG-2 gliomas, in contrast, 2/2 control animals died of tumor formation on day 14 and 15 after injection of tumor cells. The follow-up period for the surviving re-challenged animals was >3 months, MRI did not show tumor growth in any of the re-challenged rats (Table 2 and FIG. 1).

TABLE 1

Antibody titers of i.v.-treated animals

| Days after H-1PV treatment | Animal # | | |
|---|---|---|---|
| | 712 iv | 722 iv | 735 iv |
| 0 | 0 | 0 | 0 |
| 2 | | | 640 |
| 3 | | 0 | |
| 4 | | | 640 |

TABLE 1-continued

Antibody titers of i.v.-treated animals

| Days after H-1PV treatment | Animal # | | |
|---|---|---|---|
| | 712 iv | 722 iv | 735 iv |
| 5 | 20 | 0 | |
| 7 | 320 | 80 | 2560 |
| 10 | | | 5120 |
| 11 | | 640 | |
| 13 | | | 2560 |
| 14 | | | |
| 15 | | 320 | |
| 18 | | | |
| 21 | 10240 | 2560 | |

TABLE 2

Specifics of re-challenged animals

| animal | treatment | Survival after re-challenge (days) | Tumor on MRI after re-challenge |
|---|---|---|---|
| 712 | iv | >90 | none |
| 735 | iv | >90 | none |
| 703 | iv | >90 | none |
| 62 | ic | >90 | none |
| 100 | ic | >90 | none |
| 308 | ic | >90 | none |
| 378 | ic | >90 | none |

EXAMPLE 3

Figure 2B:
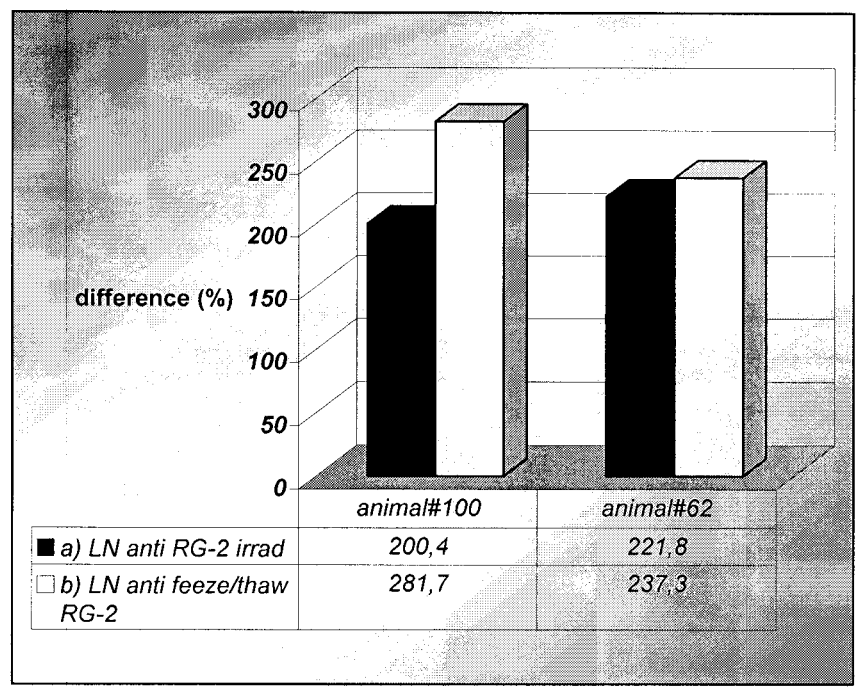

Detection of Tumor-Specific Immune Cells after Tumor Re-Challenge in Animals after Successful Parvovirus H-1PV Therapy The incubation of lymphocytes from draining lymph nodes of animals that were successfully treated with H-1PV 6 months prior to the re-challenge experiment lead to a strong increase in lymphocytic activation by RG-2 cells. This tumor-specific effect could be detected when irradiated RG-2 cells or RG-2 cells after freeze/thaw treatment were used as antigen. Absolute counts were higher after incubation of lymphocytes with irradiated RG-2 cells than with freeze/thaw treated RG-2 cells (FIG. 2a). However, the relative increase in specific lymphocyte activity compared to controls was higher after freeze/thaw treatment of RG-2 glioma cells (FIG. 2b).

EXAMPLE 4

Role of T-Cells in Glioma Suppression after Treatment of Animals with a Single Intratumoral Dose of H-1 PV Temporary CD8 cell depletion in RG2 glioma-bearing Wistar rats was tested for its effect on the fate of established gliomas after a single H-1 PV intratumoral injection. Complete regression of the glioma mass was observed in undepleted animals under these conditions. In contrast, when CD8 positive T-cells were blocked by i.p. injection of specific antibodies, H-1 PV infection failed to cause tumour suppression in depleted rats. Yet, when these tumor bearing, and infected animals were subsequently reconstituted with CD8 positive T-cells (cessation of injection of anti-CD8 antibodies), complete tumour remission took place in the absence of any additional H-1 PV injection. Importantly, in the absence of H-1 PV treatment the sole presence of T-cells was not sufficient for recovery, since no spontaneous tumour regression in glioma-bearing animals has been observed in the experimental conditions. From these data it can be concluded that the activation of a host anti-tumoral T-cell response by parvovirus H-1PV infection is essential for the successful H-1 PV-based therapy of gliomas.

EXAMPLE 5

Treatment of Pancreatic Cancer with H-1PV

Splenocytes from rats with H-1 PV-treated pancreatic tumors were transferred to naive recipients bearing the same type of tumor. The transferred immune cells were expected to passively (cytotxic lymphocytes) or actively (antigen presenting cells) protect recipients from tumor development. Indeed the adoptive transfer from H-1 PV-treated donors caused almost doubling of median survival time in these animals, compared to control recipients receiving splenocytes from rats with untreated tumors.

Tumor Model

All surgical and imaging procedures were performed under aerosol anaesthesia. Immunocompetent male Lewis rats (Janvier, Le Genest Saint Isle, France) weighting 180-200 g were used for pancreatic carcinoma implantation. A suspension of $5 \times 10^6$ cells in 200 µl phosphate-buffered saline (PBS) was prepared from subcutaneous tumors formed by implanted HA-RPC cells, and injected into the pancreatic parenchyma. Tumor progression was confined to the pancreatic tail for the first 3 weeks after implantation, leading to lymph node invasion during the fourth week. Liver metastases appeared after 5-6 weeks, and death from lung metastasis occurred at weeks 6-9.

Adoptive Transfer

Spleens were removed intact and teased apart in PBS using a sterile technique. Single-cell suspension was obtained by mincing the spleens with plunger on top of strainer followed by centrifugation at 1000 rpm for 15 minutes. Splenocytes were resuspended in supplemented RPMI 1640 and counted on a hemocytometer in trypan blue to ensure viability. Average viability was >90%. Isolated splenocytes from tumor-bearing rats treated with PBS or H-1PV were injected to the tumor-bearing recipient rats intravenously and intraperitonealy (in total $1 \times 10^7$ cells/animal) in anesthetized animals.

Results

The immunomodulating features of H-1PV infection of pancreatic tumors were assessed by using adoptive transfer of immune cells derived from the spleens of H-1PV-treated animals. Rats received an H-1PV intratumoral injection two weeks after tumor initiation in the pancreas (FIG. 3A). Three weeks later, at the point when antiviral neutralizing antibodies appeared, indicative of an ongoing immune reaction and leading to clearance of H-1PV from peripheral tissues (data not shown), the spleens of the animals were harvested and used for cell transfer to naive recipient animals bearing three week old pancreatic tumors. The splenocytes deriving from H1-1PV-treated donors could protect recipient animals leading to tumor growth retardation and a significant ($p<0.01$) prolongation of survival (152 vs 90 days) compared to cells from control donors. Three weeks after transfer the sera of recipients were evaluated by cytotoxicity protection assay for the presence of neutralizing antibodies against H-1PV. No elevation of antibody titers was observed, indicating that no viruses have been transferred together with the splenocytes (data not shown). This excluded the possibility that any H-1PV-mediated oncolytic effects could have participated in the antitumor effect observed in recipient animals.

Thus, in pancreatic cancer, as in the previously used hepatoma model, H-1PV has immunostimulating effects that can prime the immune system to react against tumors. The above-mentioned adoptive transfer experiments clearly show that the immune system of virus-treated donors can protect naive animals bearing the same tumor entity.

The invention claimed is:

1. A method of reducing the rate of recurrence of tumors in a subject, comprising administering a parvovirus to the subject wherein the parvovirus is administered in a dose sufficient to prime the immune system against a tumor and thereby reduce the rate of recurrence of the tumor wherein the parvovirus is H1 (HIPV), wherein the tumor is a pancreas tumor and wherein the dose of parvovirus is about $1 \times 10^9$ plaque-forming units.

2. The method according to claim 1, wherein said parvovirus is administered by intravenous (i.v.) or intratumoral administration.

3. The method of claim 1, wherein priming of the immune system against the tumor is assayed by testing lymphocytes from the subject after treatment with the parvovirus for immune activity against the tumor cells.

* * * * *